(12) United States Patent
Satou et al.

(10) Patent No.: US 8,585,975 B2
(45) Date of Patent: Nov. 19, 2013

(54) BLOOD GLUCOSE METER AND BLOOD GLUCOSE LEVEL MEASUREMENT METHOD

(75) Inventors: Hiroaki Satou, Nakakoma-gun (JP); Hideyuki Momoki, Nakakoma-gun (JP); Kouhei Sakaike, Higashihiroshima (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 63 days.

(21) Appl. No.: 13/496,377

(22) PCT Filed: Aug. 4, 2010

(86) PCT No.: PCT/JP2010/063198
§ 371 (c)(1),
(2), (4) Date: Mar. 15, 2012

(87) PCT Pub. No.: WO2011/033876
PCT Pub. Date: Mar. 24, 2011

(65) Prior Publication Data
US 2012/0179017 A1     Jul. 12, 2012

(30) Foreign Application Priority Data

Sep. 17, 2009  (JP) .................................. 2009-216141

(51) Int. Cl.
*G01N 25/00*   (2006.01)

(52) U.S. Cl.
USPC ......... 422/82.12; 422/500; 436/147; 600/549

(58) Field of Classification Search
USPC ......... 436/147; 422/500, 82.12; 600/301, 584
See application file for complete search history.

(56) References Cited

U.S. PATENT DOCUMENTS 6,493,069 B1     12/2002   Nagashimada et al.
8,105,841 B2 *    1/2012   Blais et al. .................... 436/147

FOREIGN PATENT DOCUMENTS

| JP | 62-054165 A   | 3/1987  |
|----|---------------|---------|
| JP | 03-063551 A   | 3/1991  |
| JP | 09-297832 A   | 11/1997 |
| JP | 2000-046834 A | 2/2000  |
| JP | 2007-010317 A | 1/2007  |

OTHER PUBLICATIONS

International Search Report (PCT/ISA/210) issued on Oct. 12, 2010, by Japanese Patent Office as the International Searching Authority for International Application No. PCT/JP2010/063198.

* cited by examiner

*Primary Examiner* — Sally Merkling
(74) *Attorney, Agent, or Firm* — Buchanan Ingersoll & Rooney PC

(57) ABSTRACT

An internal temperature sensor for measuring internal temperature of a case of the blood glucose meter is arranged inside the case of the blood glucose meter, and an external temperature sensor configured by components with low heat capacity and adapted for measuring external temperature is arranged at a position separated from the central portion of the case of the blood glucose meter. Further, a microcomputer of the blood glucose meter includes the following processing: judging whether or not the temperature fluctuation falls within the acceptable range based on the difference between the respective temperatures and, if the temperature fluctuation exceeds the acceptable range, temporarily stopping the processing until the temperature fluctuation falls within the acceptable range when in the case where the blood glucose measurement has not yet been performed, or stopping the blood glucose measurement processing when in the case where the blood glucose measurement is being performed.

6 Claims, 13 Drawing Sheets

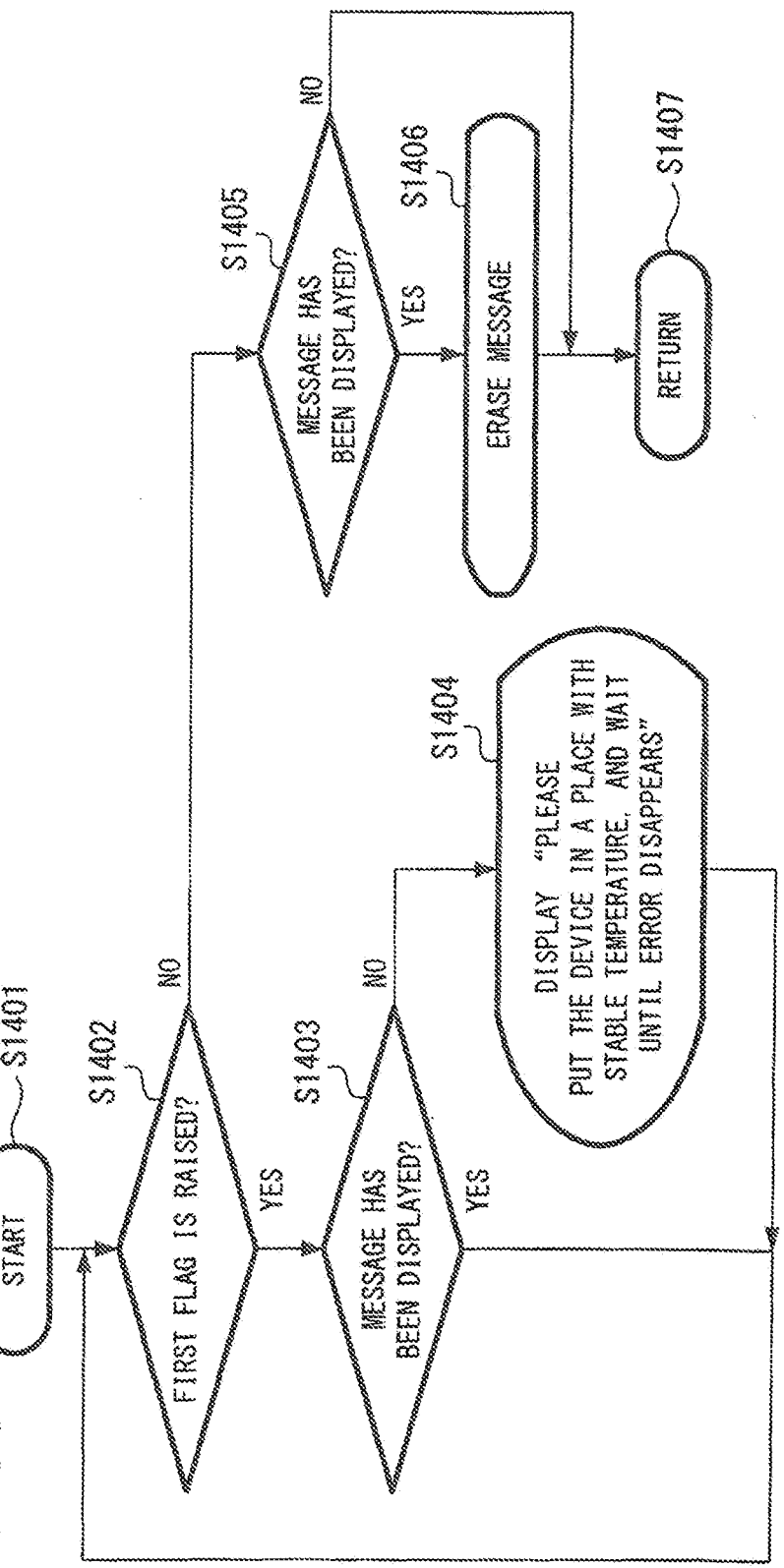

BLOOD GLUCOSE METER AND BLOOD GLUCOSE LEVEL MEASUREMENT METHOD

TECHNICAL FIELD

The present invention relates to a technique preferably applied to a blood glucose meter and a blood glucose measurement method.

More particularly, the present invention relates to a blood glucose meter and a blood glucose measurement method capable of quickly and reliably detecting fluctuation of the ambient temperature surrounding the blood glucose meter, so as to achieve accurate blood glucose measurement in a state where temperature fluctuation is stabilized.

BACKGROUND ART

As is well known, diabetes mellitus is caused by abnormal secretion of insulin from the pancreas or decreased insulin sensitivity. For a type I diabetic patient whose pancreas does not secretes insulin at all, it is necessary to measure blood glucose level of the patient before meals, and administer insulin to the patient according to the measured level.

Conventionally, in order to easily measure blood glucose level at home by a patient himself/herself or by a member of the patient's family, a miniaturized blood glucose measuring device (referred to as "blood glucose meter" hereinafter) for self-measurement has been developed, manufactured and marketed by the applicant of the present invention. Further, a blood glucose meter having various management functions and capable of dealing with a plurality of patients is being developed for hospital wards by the applicant of the present invention.

A blood glucose meter is a device for measuring blood glucose level based on a principle that a biochemical reaction is caused by contacting blood with a reagent, and thereby the glucose value is converted into color density or electrical signal. In cases that most reagents used in such blood glucose meters react with the blood, the reaction rates change according to the ambient temperature at the time when the blood glucose measurement is performed. Thus, the blood glucose meter has a built-in temperature sensor, and temperature correction calculation is performed while converting the physical value obtained when performing measurement into the blood glucose value.

Incidentally, the prior art document deemed to be related to the present invention is referred to as Patent document 1.

Patent document 1: Japanese Unexamined Patent Application Publication No. 2007-10317.

DISCLOSURE OF THE INVENTION

Problems to be Solved by the Invention

Particularly in the case of a blood glucose meter for self-measurement, the blood glucose meter is often used in an environment where rapid temperature change occurs, such as in the case where the blood glucose meter is brought from a cold room into a warm room in winter. The following description explains what will happen if the blood glucose measurement is performed in such condition.

Since the blood glucose measuring tip with the reagent infiltrated therein is mounted so that the measuring tip is exposed on the outside of the blood glucose meter, and since the measuring tip has low heat capacity, the measuring tip follows the ambient temperature relatively quickly. On the other hand, since the blood glucose meter is a device having appropriate volume, it has high heat capacity. Since the temperature sensor is mounted on the circuit board inside the blood glucose meter, it slowly follows the change of the ambient temperature. In other words, the temperature sensor can not correctly measure the ambient temperature shortly after the ambient temperature has rapidly changed. Thus, temperature correction does not correctly work, and therefore the blood glucose meter obtains erroneous blood glucose value.

As described above, there is assumed a case where temperature fluctuation occurs when using the blood glucose meter, which is unfavorable for the blood glucose measurement.

Patent document 1 discloses the technical content of a blood glucose measuring device in which a temperature sensor built into a case is arranged at a position close to an outer case body, and thereby it is possible to measure the ambient temperature and perform correct temperature correction.

However, since the heat left in the case of the blood glucose meter will affect the measurement, the temperature correction can not be correctly performed by only measuring the temperature of the outer case body.

It is preferred that the case of the blood glucose meter is acclimatized to the external temperature, i.e., the temperature of the case of the blood glucose meter becomes substantially equal to the ambient temperature.

The present invention has been made in view of the above problems, and it is an object of the present invention to provide a new and useful blood glucose meter and blood glucose measurement method capable of quickly detecting the temperature fluctuation of the ambient temperature, and controlling blood glucose measurement operation according to the temperature fluctuation.

Means for Solving the Problems

To solve the aforesaid problems, a blood glucose meter according to an aspect of the present invention includes a blood glucose measuring section adapted to, in a state where a measuring tip is mounted, spot blood onto the measuring tip, and output a signal corresponding to the glucose level of the blood; a tip mounting processing section adapted to confirm whether or not the measuring tip has been mounted on the blood glucose measuring section; a blood spotting standby processing section adapted to confirm whether or not the blood has been spotted onto the measuring tip; a measurement processing section adapted to obtain a blood glucose value based on the signal outputted from the blood glucose measuring section; a case in which the tip mounting processing section, the blood spotting standby processing section and the measurement processing section are housed; an internal temperature sensor disposed inside the case; an external temperature sensor disposed in a peripheral portion of the case separated from the internal temperature sensor; a temperature check processing section adapted to compare temperature difference between the internal temperature sensor and the external temperature sensor with a predetermined threshold to judge whether or not the change of the ambient temperature of the case is suitable for measuring blood glucose level; and a controller adapted to temporarily stop, if the temperature check processing section judges that it is not suitable for measuring blood glucose level when the tip mounting processing section or the blood spotting standby processing section is in operation, the processing of the tip mounting processing section or the processing of the blood spotting standby processing section until the temperature check processing section judges that it is suitable for measuring blood glucose level.

In other words, an internal temperature sensor for measuring the internal temperature of the case of the blood glucose meter is arranged inside the case of the blood glucose meter, and an external temperature sensor configured by components with low heat capacity and adapted for measuring the external temperature is arranged at a position separated from the central portion of the case of the blood glucose meter. Further, the blood glucose meter is configured so that it is judged whether or not the temperature fluctuation falls within the acceptable range based on the each temperature difference, and if the temperature fluctuation exceeds the acceptable range, the processing will be temporary stopped until the temperature fluctuation falls within the acceptable range in the case where the blood glucose measurement has not been performed, or the blood glucose measurement processing will be stopped in the case where the blood glucose measurement is being performed.

By configuring the blood glucose meter in the aforesaid manner, it is possible to reliably detect the temperature fluctuation surrounding the blood glucose meter, and perform blood glucose measurement in an appropriate environment.

Advantages of the Invention

According to the present invention, it is possible to provide a new and useful blood glucose meter and blood glucose measurement method capable of quickly detecting the temperature fluctuation of the ambient temperature, and controlling blood glucose measurement operation according to the temperature fluctuation.

BRIEF DESCRIPTION OF DRAWINGS

FIG. 14 is a flowchart showing exception-judging processing according to the aforesaid embodiment.

BEST MODES FOR CARRYING OUT THE INVENTION

An embodiment of the present invention will be described below with reference to FIGS. 1 to 14.

Figure 1:
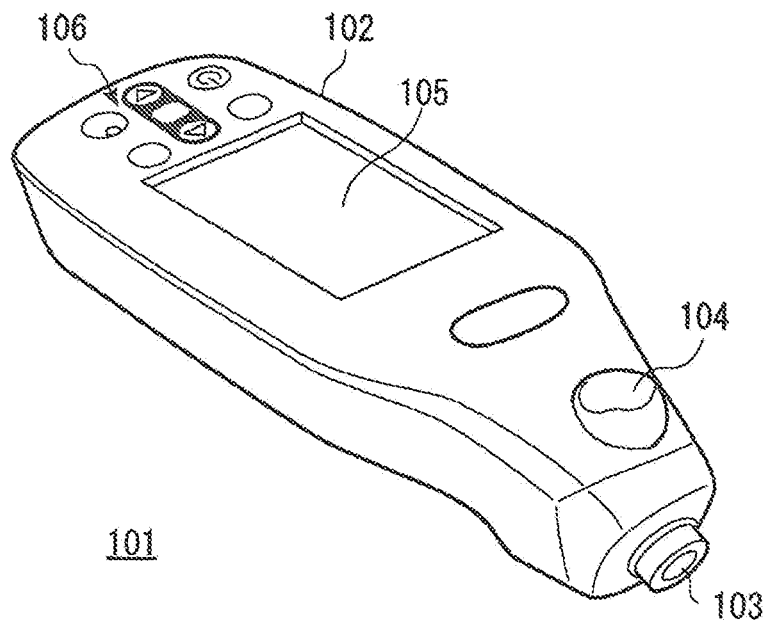
FIG. 1 is a perspective view showing the appearance of a blood glucose meter according to an embodiment of the present invention.

FIG. 1 is a perspective view showing the appearance of a blood glucose meter according to the embodiment of the present invention.

Figure 2:
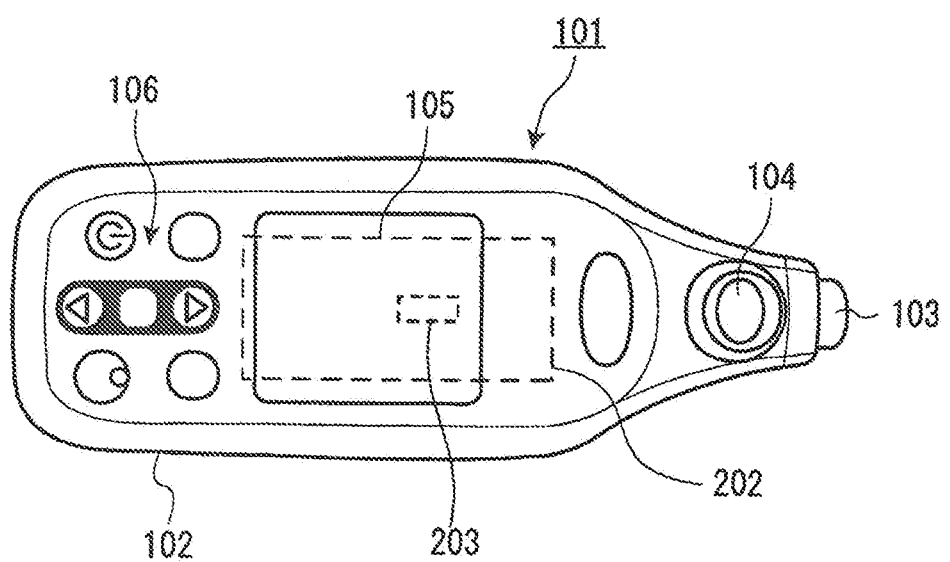
FIG. 2 is a top view of the blood glucose meter according to the aforesaid embodiment of the present invention.

FIG. 2 is a top view of the blood glucose meter according to the embodiment of the present invention.

A blood glucose meter 101 is a portable device for measuring blood glucose level. The blood glucose meter 101 is adapted to be operated by one hand of a doctor, a nurse or a patient himself/herself, just like a cellular phone, and therefore is formed so as to have a shape and weight suitable to be easily held by one hand.

The blood glucose meter 101 not only can measure blood glucose level but also, as additional functions, can perform other operations such as confirming the name and ID of a patient, storing measured value data for each patient and, if necessary, confirming appropriate drug(s) to be administered for each patient.

The blood glucose meter 101 has a case 102, which is a slender container made of synthetic resin. An optical measuring section 103 for measuring blood glucose level or the like is provided at a tip end in the longitudinal direction of the case 102. The optical measuring section 103 is a cylindrical component made of metal. A LED and a photodiode (which are to be described later) are built into the optical measuring section 103, which is also referred to as "blood glucose measuring section".

The optical measuring section 103 is formed so that a blood glucose measuring tip (referred to as "measuring tip" hereinafter) can be mounted to and dismounted from the optical measuring section 103. The used measuring tip can be dismounted from the optical measuring section 103 by operating an eject lever 104.

Further, a display panel 105, which is a LCD, for displaying the measurement result, the confirmation items and the like is arranged on the front face of the case 102. An operation panel 106 having a plurality of buttons is arranged beside the display panel 105.

Other components arranged in the blood glucose meter 101 include: a lithium-ion battery (not shown in the drawings) built into the case 102, a bar code reader unit (not shown) for reading bar code, an IrDA interface (not shown) for transmitting/receiving the patient data, the measured blood glucose data and the like. However, since these components do not directly relate to the present invention, the details thereof will not be described herein.

As shown in FIG. 2, although not invisible from the outside of the blood glucose meter 101, a circuit board 202 (which is a printed board) is built into the meter body. A known microcomputer is mounted on the circuit board 202. The microcomputer, which is powered by the lithium-ion battery, is adapted to receive an operating command signal from the operation panel 106, drive the LED arranged in the optical measuring section 103, perform predetermined blood glucose measurement through the photodiode, and display measurement result and the like on the display panel 105.

The basic blood glucose measuring mechanism of the blood glucose meter 101 is identical to that of the prior art, and therefore the outline will be briefly described below.

A measuring tip is mounted on the optical measuring section 103 to suck the blood of the object person to be measured into the measuring tip. A test paper 511 formed of a porous membrane, such as a polyethersulfone membrane, is built into the measuring tip. Further, when the blood sucked into the measuring tip reaches the test paper 511, the glucose in the blood will react with the reagent contained in the test paper 511 so as to develop a color. The chromogenic reaction will take a time from several seconds to over ten seconds, and the chromogenic reaction is affected according to the ambient temperature.

The light emitted by the LED (the light-emitting element) is radiated onto the test paper, and the light reflected from the test paper 511 is received by the photodiode (the light-receiving element). After a predetermined reaction time has elapsed, an analog intensity signal of the received light obtained from the light-receiving element is converted into a digital value, and thereafter the digital value is converted into the blood glucose value to be displayed on the display panel 105.

Incidentally, instead of being limited to the aforesaid optical measurement method in which the chromogenic reagent is used, the mechanism on the blood glucose measuring side may also be a mechanism conventionally used to measure blood glucose level, such as an electrochemical sensor method or the like.

As described above, when measuring blood glucose level, the reaction time of the reagent contained in the test paper changes according to the ambient temperature. For this reason, reaction correction values with respect to the ambient temperature are stored in a ROM, which is a constituent element of the microcomputer inside of blood glucose meter 101. Further, the program of the microcomputer stored in the ROM is constituted so that the ambient temperature when measuring blood glucose level is detected to calculate suitable measured value.

However, the correction value can not be correctly derived if the ambient temperature changes during the measurement. Thus, there is a very high risk that an incorrect blood glucose value might be derived. In other words, the ambient temperature must not change during the measurement. Obviously, if there was a change in ambient temperature immediately before the measurement, the blood glucose measurement processing can not be performed until the change has quieted down.

In order to detect that the ambient temperature of the blood glucose meter 101 is stable, the blood glucose meter 101 is provided with two temperature measuring elements.

One of the temperature measuring elements is an external temperature sensor for measuring the ambient air temperature (referred to as "external temperature" hereinafter). The external temperature sensor is disposed at a position separated from the central portion of the case of the blood glucose meter 101 and thermally independent from the case.

The other one of the temperature measuring elements is an internal temperature sensor for measuring the temperature inside the case (referred to as "internal temperature" hereinafter). The internal temperature sensor is disposed in the central portion of the case of the blood glucose meter 101.

If the two temperature sensors do not change even a predetermined period of time has elapsed and if difference between the two temperature sensors is small, then it can be judged that the whole case of the blood glucose meter 101 has "acclimatized" to the external temperature (i.e., it can be judged that the difference between the temperature outside the case of the blood glucose meter 101 and the temperature inside the case of the blood glucose meter 101 is small enough to correctly measure blood glucose level).

An internal temperature thermistor 203 (which is the internal temperature sensor) is mounted on the circuit board 202 in the same manner as other circuit components constituting the microcomputer and the like.

On the other hand, an external temperature thermistor 307 (which is the external temperature sensor) is arranged in the optical measuring section 103.

Figure 3:
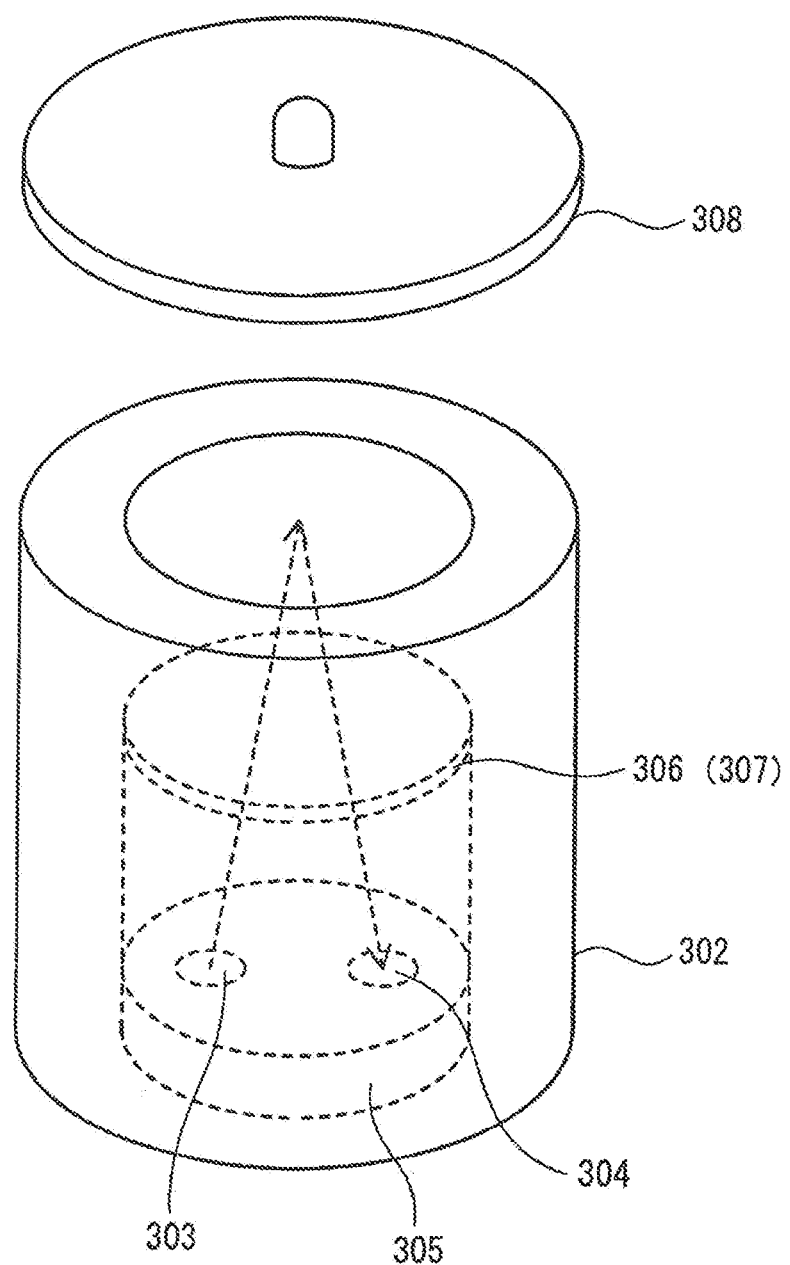
FIG. 3 is a schematic illustration of an optical measuring section.

FIG. 3 is a schematic illustration of the optical measuring section 103.

The optical measuring section 103 includes a tube 302, a LED 303, a photodiode 304, a base 305 and a glass window 305, wherein the LED 303, the photodiode 304, the base 305 and the glass window 306 are housed in the tube 302.

Inside the tube 302, which is made of a metal such as a stainless steel or the like, the LED 303 and the photodiode 304 are mounted on the base 305. For dust-proof purpose, the base 305 is shut off from the ambient air by the glass window 306, which is made of a thin glass plate. A platinum wire is printed on the glass window 306, and the wire and the glass window constitute the external temperature thermistor 307.

In order to quickly and suitably measure the external temperature, the external temperature thermistor 307 needs to have a small heat capacity. Thus, the glass plate configuring the external temperature thermistor 307 is formed to a size of 6 mm in diameter and 0.5 mm in thickness. The heat capacity of the glass plate is about 4 mJ/K.

A holding mechanism (not shown in the drawings) is incorporated into the tube 302, the holding mechanism being adapted to enable the measuring tip 308 to be mounted and dismounted. When the measuring tip 308 is mounted, the test paper 511 is disposed so as to face the glass window 306.

[Hardware]

Figure 4:
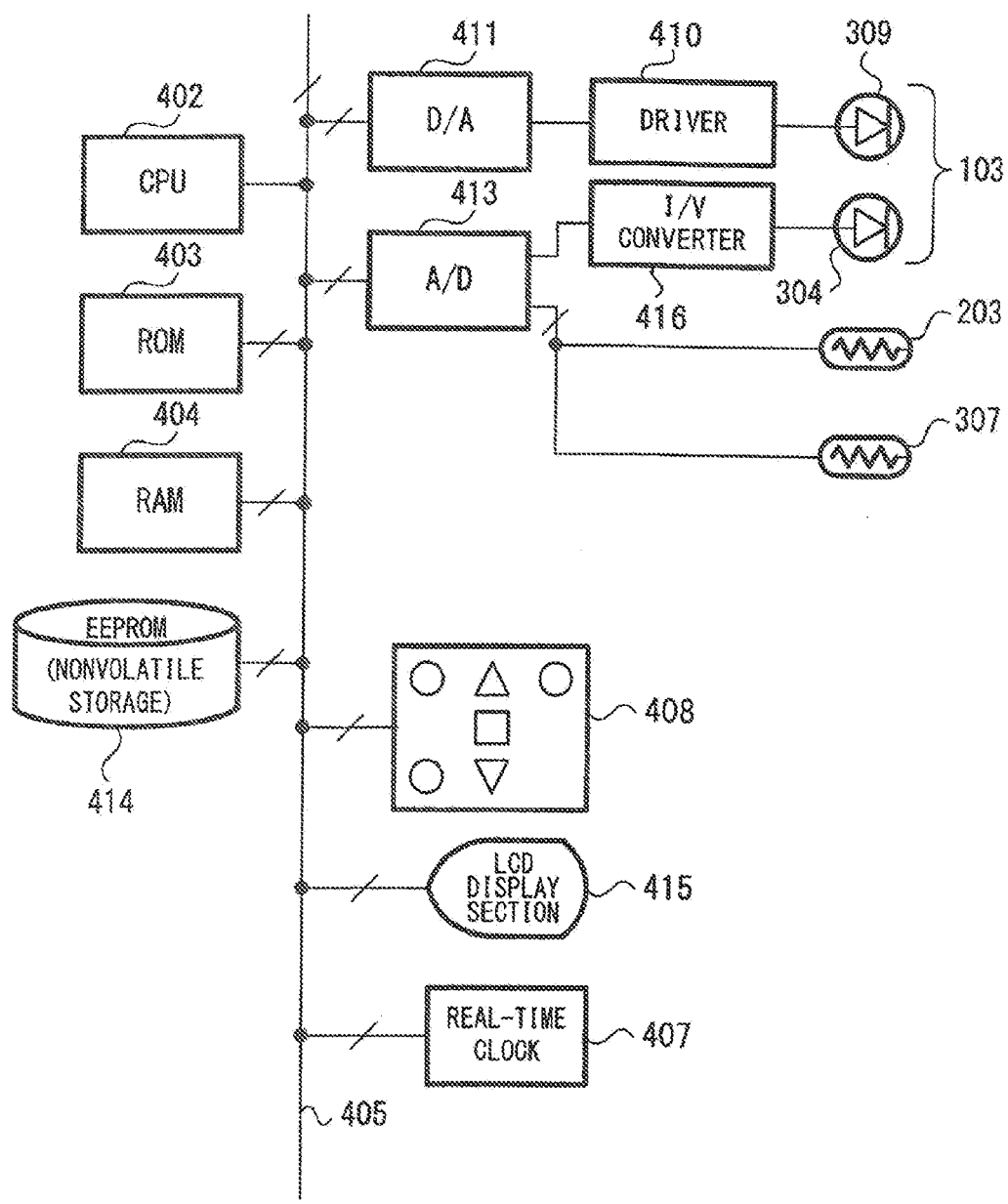
FIG. 4 is an internal block diagram of the blood glucose meter.

FIG. 4 is an internal block diagram of the blood glucose meter 101.

The blood glucose meter 101 is a system having a microcomputer, and includes a CPU 402, a ROM 403, a RAM 404, and a bus 405, wherein the bus 405 connects the CPU 402, the ROM 403 and the RAM 404. In addition to the aforesaid components, a component for mainly providing data input function and a component for mainly providing data output function are connected to the bus 405.

The optical measuring section 103 (which is important to the blood glucose meter 101) for acquiring blood glucose measurement data, the internal temperature thermistor 203 and the external temperature thermistor 307 both for acquiring temperature data, a real-time clock 407, and a button operating portion 408 (which is the operation panel 106) are provided to the component for providing the data input function of the blood glucose meter 101.

A driver 410 for driving the LED 303 to emit light is connected to the LED 303, which constitutes the optical measuring section 103. The driving of the driver 410 is controlled by a D/A converter 411.

An A/D converter 413 is connected to the photodiode 304, which constitutes the optical measuring section 103, through an I/V converter 416.

Since it is necessary for the LED 303 to radiate light of proper intensity to the test paper 511 of the measuring tip 308, the LED 303 is controlled so that it emits light based on emission intensity data previously stored in a nonvolatile storage 414 (which is to be described later). In other words, the emission intensity data is read out from the nonvolatile storage 414, and converted into an analog voltage signal by the D/A converter 411, and thereafter the power of the analog voltage signal is amplified by the driver 410 to drive the LED 303 to emit light.

The light emitted by the LED 303 is radiated onto the test paper 511 of the measuring tip 308, and the light reflected by the test paper 511 is detected by the photodiode 304.

The signal current of the photodiode 304, which varies according to the intensity of the light received by the photodiode 304, is converted into a signal voltage by the I/V converter 416, and further, the signal voltage is converted into numerical data by the A/D converter 413. The converted numerical data is recorded in predetermined regions of both the RAM 404 and the nonvolatile storage 414.

Further, the blood glucose meter 101 is provided with the internal temperature thermistor 203 and the external temperature thermistor 307, and the external temperature surrounding the blood glucose meter 101 and the internal temperature of the blood glucose meter 101 can be measured based on the changes in resistances of these thermistors. Similar to the photodiode 304, the resistances of the thermistors are converted into numeric values by the A/D converter 413, and the numeric data is recorded in predetermined regions of both the RAM 404 and the nonvolatile storage 414. Incidentally, since it is not necessary to measure the intensity of the received light and the air temperature at the same time, the A/D converter 413 is shared by the photodiode 304 and the thermistors in a time-sharing manner.

The real-time clock 407 is a known IC adapted to provide a date and time data output function, and is mounted on many microcomputers and personal computers as standard.

In the blood glucose meter 101 according to the embodiment of the present invention, since it is necessary to associate the patient data and blood glucose value with the date and time information at the time when the measurement is performed and store the data in the nonvolatile storage 414, the real-time clock 407 is provided.

A LCD display section 415 (which is the display panel 105) is provided as the component for providing the data output function of the blood glucose meter 101.

Various screens are displayed on the LCD display section 415 by the program stored in the ROM 403 and executed by the CPU 402.

Among the components constituting the microcomputer in the blood glucose meter 101, the nonvolatile storage 414, which constituted by an EEPROM, is adapted to provide data storage function, in addition to the data input/output function. Patient information, setting data of the blood glucose meter 101, accuracy test data and the like are stored in the nonvolatile storage 414. The data stored in the nonvolatile storage 414 is exchanged with an external device through an infrared interface, a wireless interface or the like (these are not shown in the drawings).

[Software]

Figure 5:
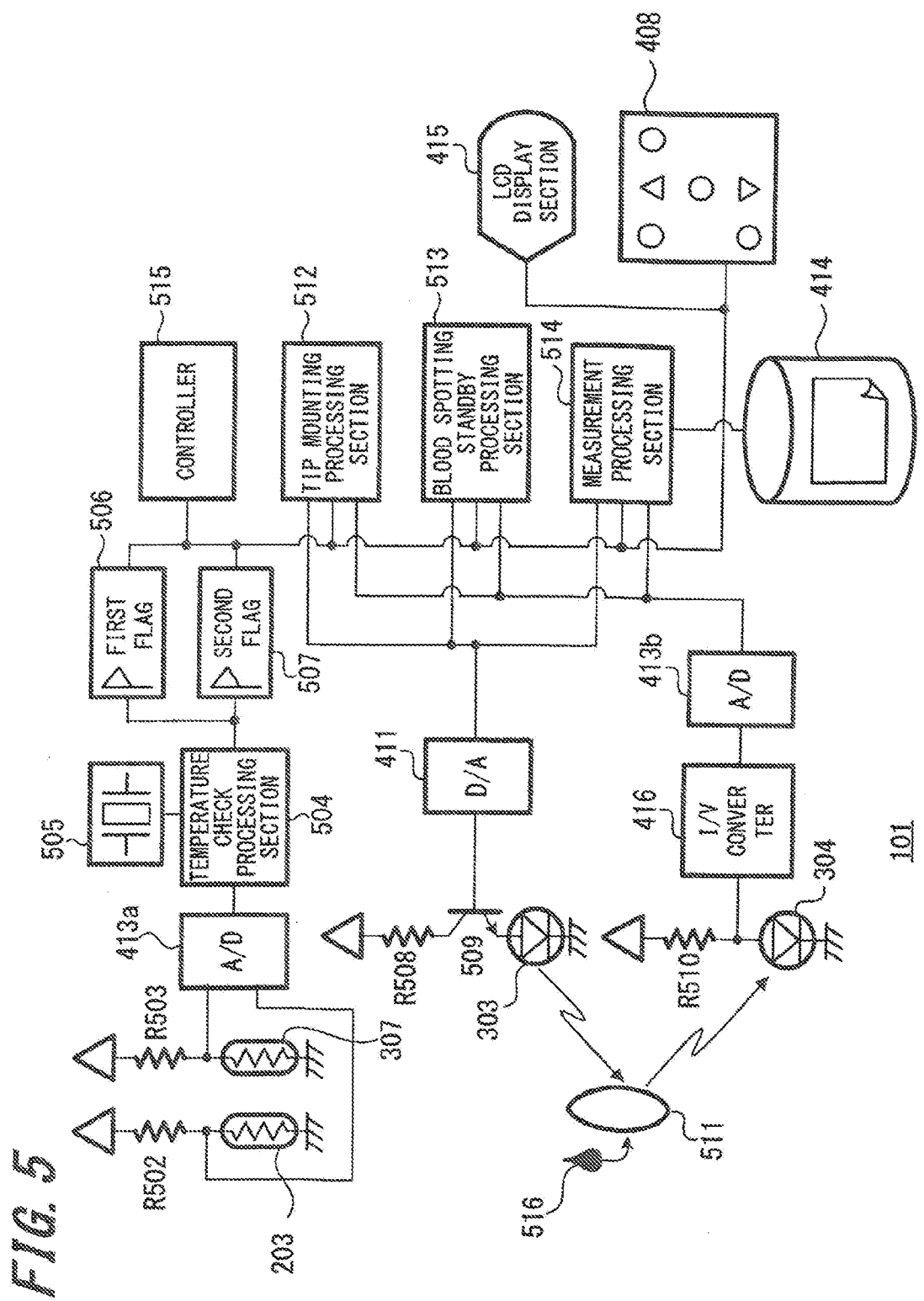
FIG. 5 is a functional block diagram of the blood glucose meter.

FIG. 5 is a functional block diagram of the blood glucose meter 101. FIG. 5 focuses on the functions provided by the microcomputer.

The voltage of the power source is applied to the internal temperature thermistor 203 and the external temperature thermistor 307 respectively through a voltage-dividing resistor R502 and a voltage-dividing resistor R503. As is well known, the resistance of a thermistor changes according to the ambient temperature, and therefore the voltage between the both terminals of the thermistor changes according to the change of the resistance.

An A/D converter 413a converts the voltage between the both terminals of the external temperature thermistor 307 and the voltage between the both terminals of the internal temperature thermistor 203 into digital data.

Incidentally, the A/D converter 413a and an A/D converter 413b (which is to be described later) are identical to the A/D converter 413 shown in FIG. 4. The functions of the single A/D converter 413, which is functionally shared in a time-sharing manner, will be respectively described as the A/D converter 413a for the thermistors and as the A/D converter 413b for the photodiode.

Upon receiving an interrupt clock outputted once each second from an interrupt clock generator 505, a temperature check processing section 504 performs temperature check processing based on the data of the external temperature thermistor 307 and the internal temperature thermistor 203. The result of the temperature check processing is written to a first flag 506 and a second flag 507, which are flag variables provided in the RAM.

When the temperature check processing section 504 judges that the ambient temperature is in a stable state, which is a requirement for performing the blood glucose measurement, the first flag 506 will be set to logical "false" (i.e., the flag will be lowered). In contrast, when the temperature check processing section 504 judges that the ambient temperature exceeds the fluctuation range required for performing the blood glucose measurement, the first flag 506 will be set to logical "true" (i.e., the flag will be raised).

In the case where the temperature check processing section 504 judges that temperature fluctuation occurs during the blood glucose measurement, and such temperature fluctuation exceeds the fluctuation range required for performing the blood glucose measurement, the second flag 507 will be set to logical "true". While in other cases, the second flag 507 will be set to logical "false".

The power source voltage is applied to the LED 303 through a voltage-dividing resistor R508 and a driving transistor 509. The D/A converter 411 is connected to the base of the driving transistor 509, and whether or not the LED 303 should emit light, and brightness of the LED 303 are controlled according to the change in base current.

The power source voltage is applied to the photodiode 304 through a voltage-dividing resistor R510. Upon receiving the reflected light of the LED 303 from the test paper 511 of the measuring tip 308, the photodiode 304 generates a signal current. The signal current is converted into a voltage by the I/V converter 416, and the voltage is further converted into digital data by the A/D converter 413b.

A tip mounting processing section 512 verifies whether or not the measuring tip 308 has been mounted on the optical measuring section 103 and, if yes, whether the measuring tip 308 has been normally mounted on the optical measuring section 103. Thus, the tip mounting processing section 512 controls the driving of the LED 303 through the D/A converter 411, and acquires data of the amount of the reflected light of the photodiode 304 from the A/D converter 413b to judge the mounting state of the measuring tip 308.

A blood spotting standby processing section 513 verifies whether or not the blood has been spotted onto the test paper 511 of the measuring tip 308. Thus, the blood spotting standby processing section 513 controls the driving of the LED 303 through the D/A converter 411, and acquires the data of the amount of the reflected light of the photodiode 304 from the A/D converter 413b to judge the state of the test paper 511 of the measuring tip 308.

A measurement processing section 514 performs the blood glucose measurement. Thus, the measurement processing section 514 controls the driving of the LED 303 through the D/A converter 411, and acquires the data of the reflected light of the photodiode 304 from the A/D converter 413b to calculate the blood glucose value after a predetermined time has elapsed from the start of the measurement processing. Further, if the measurement processing has been normally completed, the measurement data will be recorded in the nonvolatile storage 414.

A controller 515 continues to monitor the states of the first flag 506 and the second flag 507, and controls the executions of the tip mounting processing section 512, the blood spotting standby processing section 513 and the measurement processing section 514.

Necessary character(s), figure(s) and/or the like are displayed on the LCD display section 415 by the tip mounting processing section 512, the blood spotting standby processing section 513, the measurement processing section 514 and the controller 515.

The button operating portion 408 is a collection of push-button switches. Upon receiving input operation of the button operating portion 408, mainly the controller 515 performs operation control. The button operating portion 408 is provided with a cursor button, an enter button, a function button, and a power button.

[Processing Flow]

The operation flow of the blood glucose meter 101 will be described below with reference to FIGS. 6 to 9.

Figure 6:
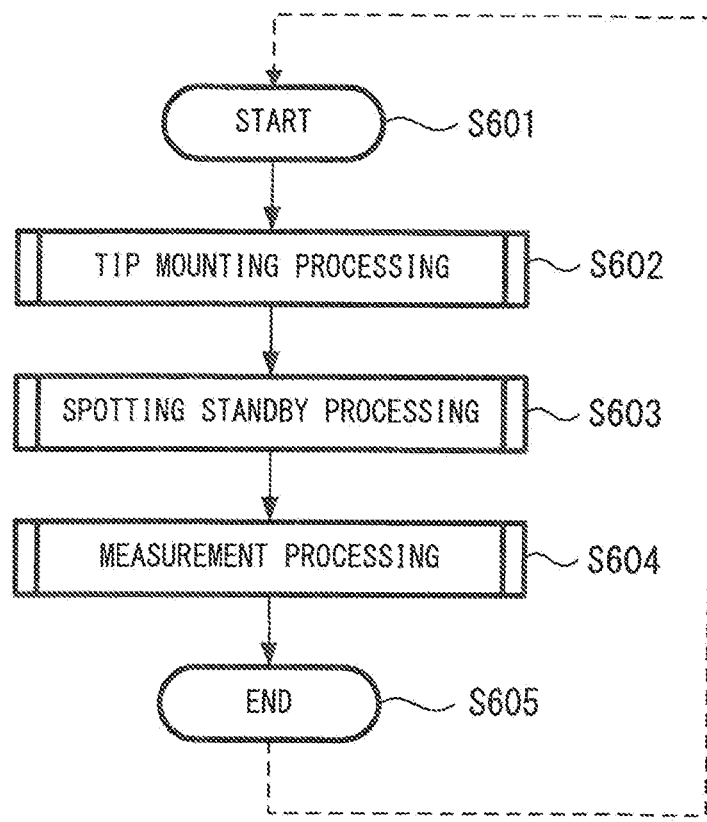
FIG. 6 is a flowchart showing overall processing of the blood glucose meter.

FIG. 6 is a flowchart showing overall processing of the blood glucose meter 101.

When processing is started (S601), the blood glucose meter 101 performs a tip mounting processing (S602) which confirms whether or not the measuring tip 308 has been normally mounted.

When the tip mounting processing has been completed, the blood glucose meter 101 performs a blood spotting standby processing (S603) which confirms whether or not the blood of the patient has been spotted onto the test paper 511 of the measuring tip 308.

When the blood spotting standby processing has been completed, the blood glucose meter 101 performs a measurement processing (S604) which measures the blood glucose level based on the amount of the reflected light at the time when a predetermined period has elapsed, and terminates the sequence of processing (S605).

After the sequence of processing has been completed (S605), if next measurement is to be performed, the overall processing will be started again (S601).

Figure 7:
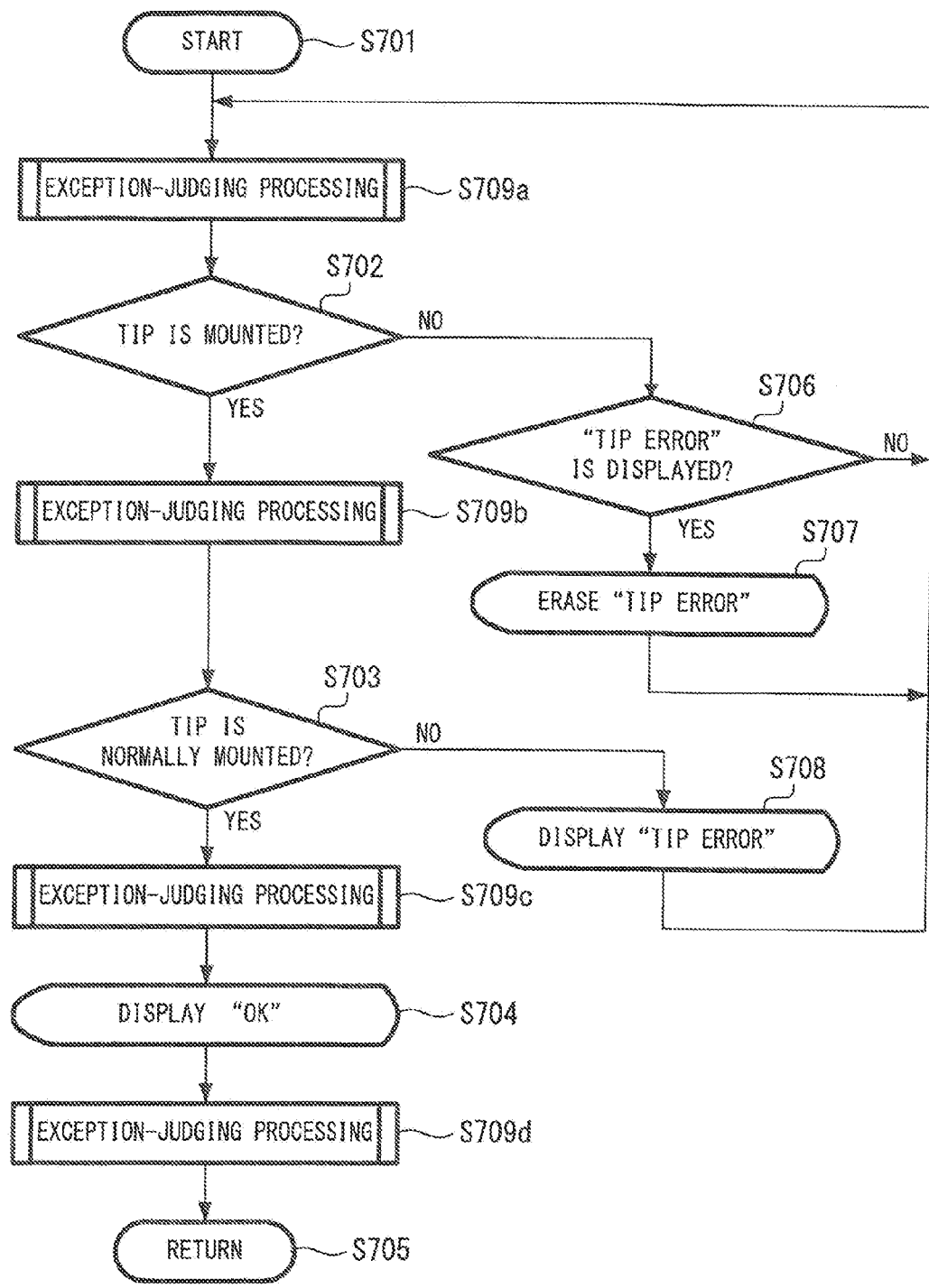
FIG. 7 is a flowchart showing tip mounting processing.

FIG. 7 is a flowchart of the tip mounting processing. FIG. 7 shows the processing details of the tip mounting processing S602 in FIG. 6 and the processing details of the tip mounting processing section 512 in FIG. 5.

For convenience of description, the processing flow will be described below first with steps S709a, S709b, S709c and S709d of FIG. 7, which are each an exception-judging processing, omitted.

When processing is started (S701), the tip mounting processing section 512 confirms whether or not the measuring tip 308 has been mounted on the optical measuring section 103 (S702). To be specific, the tip mounting processing section 512 outputs the driving control data of the LED 303 to the D/A converter 411, and controls the LED 303 through the driver so that the LED 303 intermittently emits light. The voltage signal, which is obtained based on the reflected light, obtained from the photodiode 304 is converted into the data of the reflected light through the A/D converter 413b. The tip mounting processing section 512 compares the data of the reflected light with a predetermined threshold to judge whether or not the measuring tip 308 has been mounted on the optical measuring section 103.

If the tip mounting processing section 512 judges that the measuring tip 308 has been mounted on the optical measuring section 103 in the step S702 ("Yes" in the step S702), the tip mounting processing section 512 will confirm whether or not the measuring tip 308 has been normally mounted on the optical measuring section 103 (S703). If it is judged that the measuring tip 308 has been normally mounted on the optical measuring section 103 ("Yes" in the step S703), the tip mounting processing section 512 will display a character string "OK" on the LCD display section 415 (S704), and then terminate the sequence of processing and return to the overall processing (S705).

If the tip mounting processing section 512 judges that the measuring tip 308 has not been mounted on the optical measuring section 103 in the step S702 ("No" in the step S702), the tip mounting processing section 512 will confirm whether or not a character string "tip error" has been displayed on the LCD display section 415 (S706). If the character string "tip error" has been displayed on the LCD display section 415 ("Yes" in the step S706), the tip mounting processing section 512 will erase the character string "tip error" displayed on the LCD display section 415 (S707), and confirm the tip mounting state again (S702).

If the tip mounting processing section 512 judges that the measuring tip 308 has not been normally mounted on the optical measuring section 103 in the step S703 ("No" in the step S703), the tip mounting processing section 512 will display the character string "tip error" on the LCD display section 415 (S708), and confirm the tip mounting state again (S702).

There are three mounting states of the measuring tip 308 to the optical measuring section 103 as below.

The first is a state where the measuring tip 308 has not been mounted on the optical measuring section 103 (i.e., an unmounted state), and in such state, the judgment made by the step S702 is "No".

The second is a state where the measuring tip 308 has been mounted on the optical measuring section 103, but has not been normally mounted on the optical measuring section 103 (i.e., an imperfectly-mounted state), and in such state, the judgment made by the step S702 is "Yes", but the judgment made by the step S703 is "No".

The third is a state where the measuring tip 308 not only has been mounted, but also has been normally mounted on the optical measuring section 103 (i.e., a perfectly-mounted state), and in such state, not only the judgment made by the step S702 is "Yes", but also the judgment made by the step S703 is "Yes".

In order to erase the tip error, the measuring tip 308 is once dismounted from the optical measuring section 103 and then mounted again on the optical measuring section 103, and therefore if "tip error" is displayed on the LCD display section 415 in the unmounted state, the "tip error" should be erased at this point.

The description above is a typical processing flow of the tip mounting processing. However, exception-judging processing S709a, S709b, S709c and S709d are respectively disposed immediately before the step S702, immediately before the step S703, immediately before the step S704, and immediately after the step S704. All the exception-judging processing S709a, S709b, S709c and S709d are subroutines having the same processing details, and such processing details is performed by the controller 515. The details of the exception-judging processing will be described later with reference to FIG. 12.

Figure 8:
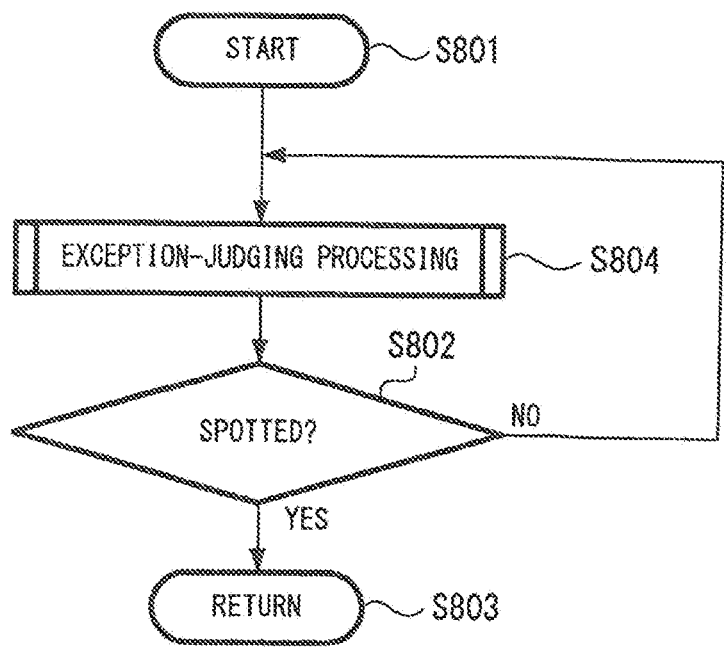
FIG. 8 is a flowchart showing blood spotting standby processing.

FIG. 8 is a flowchart showing the blood spotting standby processing. FIG. 8 shows the details of the blood spotting standby processing S603 in FIG. 6 and the details of the blood spotting standby processing section 513 in FIG. 5.

For convenience of description, the processing flow will be described below first with the step S804 of FIG. 8, which is the exception-judging processing, omitted.

When processing is started (S801), the blood spotting standby processing section 513 confirms whether or not the blood has been spotted onto the test paper 511 of the measuring tip 308 (S802). To be specific, the blood spotting standby processing section 513 outputs the driving control data of the LED 303 to the D/A converter 411, and controls the LED 303 through the driver so that the LED 303 intermittently emits light. The voltage signal, which is obtained based on the reflected light, obtained from the photodiode 304 is converted into the data of the reflected light through the A/D converter 413b. The blood spotting standby processing section 513 compares the data of the reflected light with a predetermined threshold to judge whether or not the blood has been spotted onto the test paper 511.

If the blood spotting standby processing section 513 judges that the blood has been spotted onto the test paper 511 in the step S802 ("Yes" in the step S802), the blood spotting standby processing section 513 will terminate the sequence of processing and return to the overall processing (S803).

If the blood spotting standby processing section 513 judges that the blood has not been spotted onto the test paper 511 in the step S802 ("No" in the step S802), the blood spotting standby processing section 513 will confirm whether or not the blood has been spotted onto the test paper 511 again (S802). In other words, the blood spotting standby processing section 513 loops until the blood spotting can be confirmed.

The description above is a typical processing flow of the blood spotting standby processing. However, there is a step S804 (exception-judging processing) immediately before the step S802. The step S804 is a subroutine having the same processing details as those of the exception-judging processing S709a, S709b, S709c and S709d of FIG. 7, and the step S804 will be described later in more detail with reference to FIG. 12.

Figure 9:
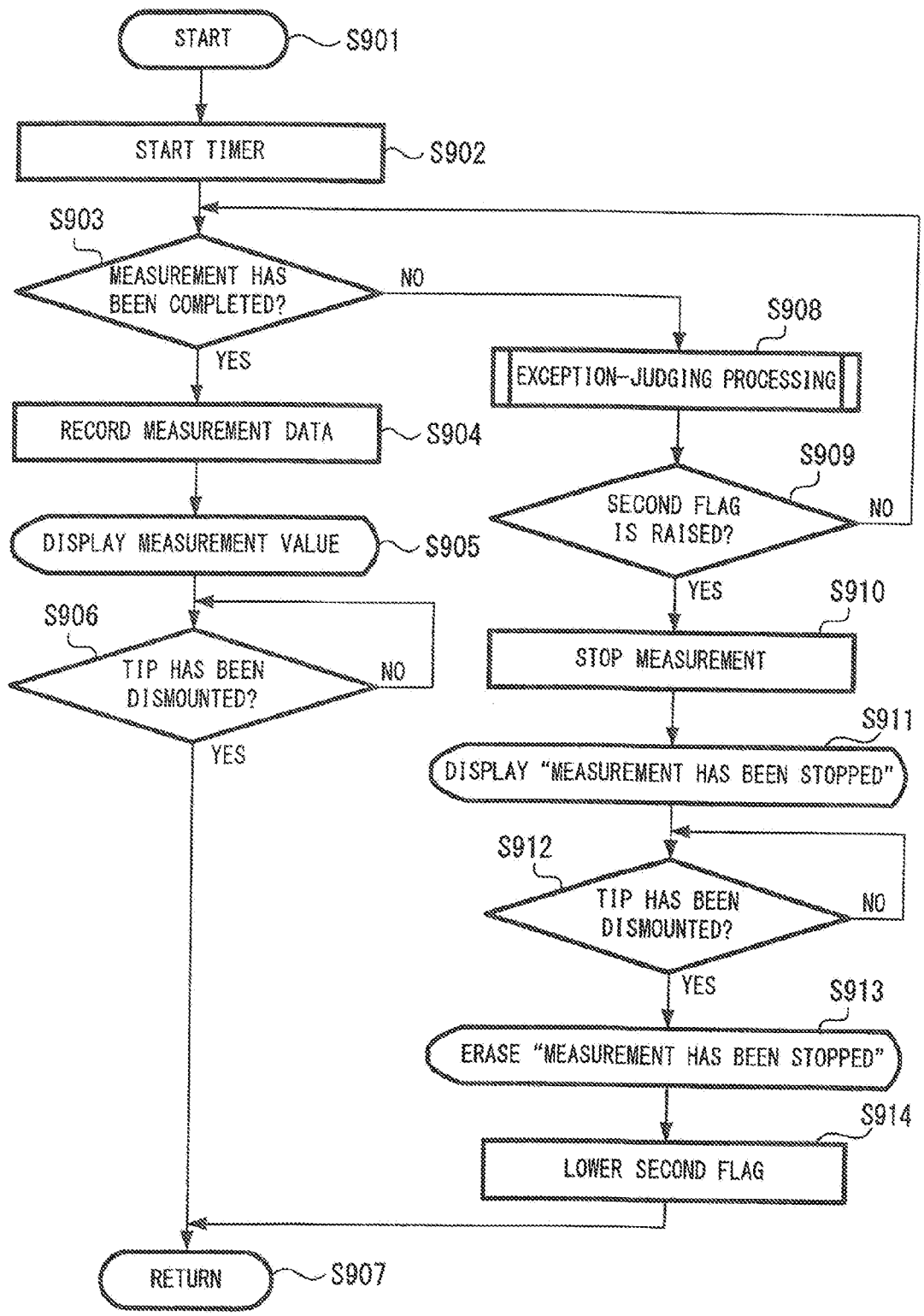
FIG. 9 is a flowchart showing measurement processing.

FIG. 9 is a flowchart showing the measurement processing. FIG. 9 shows the processing details of the measurement processing S604 in FIG. 6 and the processing details of the measurement processing section 514 in FIG. 5.

When processing is started (S901), the measurement processing section 514 starts a built-in timer (not shown in the drawings) for counting the time necessary to perform the measurement (S902). Next, based on the time indicated by the timer (i.e., the measurement time), the measurement processing section 514 confirms whether or not the measurement has been completed (S903).

If it is confirmed in the step S903 that the measurement has been completed based on the measurement time ("Yes" in the step S903), the measurement processing section 514 will move forward with the processing to be performed in the case where the measurement processing of the blood glucose level has been normally completed.

The voltage signal, which is obtained based on the reflected light, obtained from the photodiode 304 is converted into digital data by the A/D converter 413b, and the measurement processing section 514 reads the digital data and performs a predetermined arithmetic processing to obtain measurement data. The measurement processing section 514 records such measurement data in the nonvolatile storage 414 (S904).

Next, the measurement processing section 514 displays the measurement data on the LCD display section 415 as the blood glucose measurement value (S905). Further, the measurement processing section 514 continues to confirm whether or not the used measuring tip 308 has been dismounted from the optical measuring section 103 (S906). To be specific, the measurement processing section 514 outputs the driving control data of the LED 303 to the D/A converter 411, and controls the LED 303 through the driver so that the LED 303 intermittently emits light. The voltage signal, which is obtained based on the reflected light, obtained from the photodiode 304 is converted into the data of the reflected light through the A/D converter 413b. The measurement processing section 514 compares the data of the reflected light with a predetermined threshold to judge whether or not the measuring tip 308 has been dismounted from the optical measuring section 103.

If it is confirmed that the measuring tip 308 has been dismounted ("Yes" in the step S906), the measurement processing section 514 will terminate the sequence of processing and return to the overall processing (S907).

If it is confirmed in the step S903 that the measurement has not been completed based on the measurement time ("No" in the step S903), the measurement processing section 514 will confirm whether or not the second flag 507 is raised ("No" in the step S909) through the exception-judging processing (S908), and then confirm the measurement time again (S903).

The second flag 507 is a flag set by the temperature check processing section 504 in the case where, in the exception-judging processing of the step S908, the temperature fluctuation exceeds the acceptable range during the time while the blood glucose is being measured. Thus, if the temperature fluctuation is within the acceptable range, the measurement processing section 514 will pass through the steps S908 and S909 to substantially perform the loop processing of the step S903.

If it is confirmed in the step S909 that the second flag 507 is raised ("Yes" in the step S909), the measurement processing section 514 will move forward with the processing to be performed in the case where the measurement processing of the blood glucose level has failed.

First, the measurement processing section 514 stops the measurement operation (S910). To be specific, the measurement processing section 514 stops the timer started in the step S902 to stop outputting the driving control data of the LED 303 having been outputted to the D/A converter 411. Further, the measurement processing section 514 also stops the operation of the A/D converter 413b to stop reading the data based on the output current of the photodiode 304. Further, the measurement processing section 514 records the information indicating "measurement failure" to the nonvolatile storage 414.

Next, the measurement processing section 514 displays a character string "measurement has been stopped" on the LCD display section 415 (S911). Further, the measurement processing section 514 continues to confirm whether or not the used measuring tip 308 has been dismounted from the optical measuring section 103 (S912). Since such processing is identical to that of the step S906, the description thereof will be omitted herein.

If it is confirmed that the measuring tip 308 has been dismounted ("Yes" in the step S912), the measurement processing section 514 will erase the character string "measurement has been stopped" displayed on the LCD display section 415 (S913). Further, the measurement processing section 514 lowers the second flag 507 (S914), terminates the sequence of processing and returns to the overall processing (S907).

Figure 10:
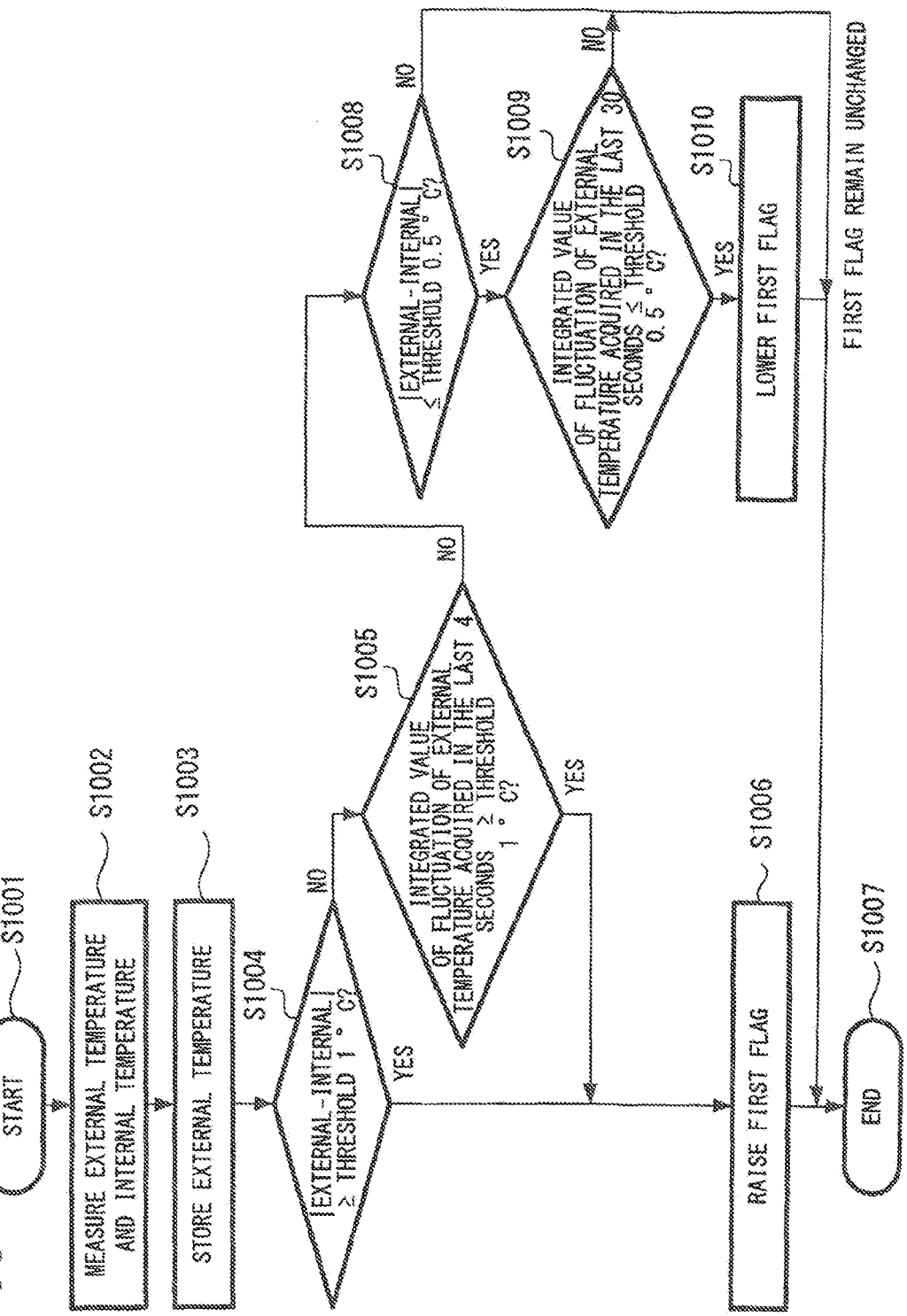
FIG. 10 is a flowchart showing temperature check processing.

FIG. 10 is a flowchart showing the temperature check processing. The temperature check processing is the processing details of the temperature check processing section 504 shown in FIG. 5.

As has been described with reference to FIG. 5, upon receiving the interrupt clock outputted once each second from an interrupt clock generator 505, the temperature check processing section 504 performs the temperature check processing. In other words, the temperature check processing shown in FIG. 10 is an interrupt processing performed once each second, without any relation with the overall processing shown in FIG. 6.

When starting performing the temperature check processing upon receiving the interrupt clock (S1001), the temperature check processing section 504 measures the external temperature and the internal temperature (S1002). To be specific, the temperature check processing section 504 converts the voltages of the external temperature thermistor 307 and the internal temperature thermistor 203 into data through the A/D converter 413b, and obtains external temperature data and internal temperature data based on the converted data.

Next, the temperature check processing section 504 stores the obtained external temperature data in a memory not shown in the drawings (S1003).

Next, the temperature check processing section 504 subtracts the internal temperature data from the external temperature data to obtain the absolute value of the result of the subtraction (i.e., the temperature difference between the external temperature and the internal temperature). The temperature check processing section 504 confirms whether the temperature difference is equal to or larger than 1° C., which is a threshold (S1004).

If the temperature difference in the step S1004 is smaller than the threshold 1° C. ("No" in the step S1004), the temperature check processing section 504 will integrate the fluctuation of the external temperature acquired in the last 4 seconds to calculate the integrated value, and confirm whether the integrated value is equal to or larger than the threshold 1° C. (S1005).

If the condition of either the step S1004 or the step S1005 is satisfied ("Yes" in the step S1004, or "Yes" in the step S1005), the temperature check processing section 504 will raise the first flag 506 (S1006) and terminate the sequence of processing (S1007).

The steps S1004 and S1005 are each a step of verifying whether or not the temperature fluctuation exceeds the acceptable range, and the conditions of the both steps are connected with each other by "OR" condition.

If the integrated value in the step S1005 is smaller than the threshold 1° C. ("No" in the step S1005), the temperature check processing section 504 will confirm whether the temperature difference between the external temperature and the internal temperature calculated in the step S1004 is equal to or smaller than 0.5° C. (S1008).

If it is confirmed in the step S1008 that the temperature difference is equal to or smaller than 0.5° C., which is a threshold ("Yes" in the step S1008), the temperature check processing section 504 will integrate the fluctuation of the external temperature acquired in the last 30 seconds to calculate the integrated value, and confirm whether the integrated value is equal to or smaller than the threshold 0.5° C. (S1009).

If the condition of the step S1008 and the condition of the step S1009 are both satisfied ("Yes" in the step S1009), the temperature check processing section 504 will lower the first flag 506 (S1010) and terminate the sequence of processing (S1007).

The steps S1008 and S1009 are each a step of verifying whether or not the temperature fluctuation falls within the acceptable range, and the conditions of the both steps are connected with each other by "AND" condition.

Incidentally, in each case of the step S1008 and the step S1009, if the condition is not satisfied, the temperature check processing section 504 will terminate the sequence of processing without changing the first flag 506 (S1007).

Figure 11:
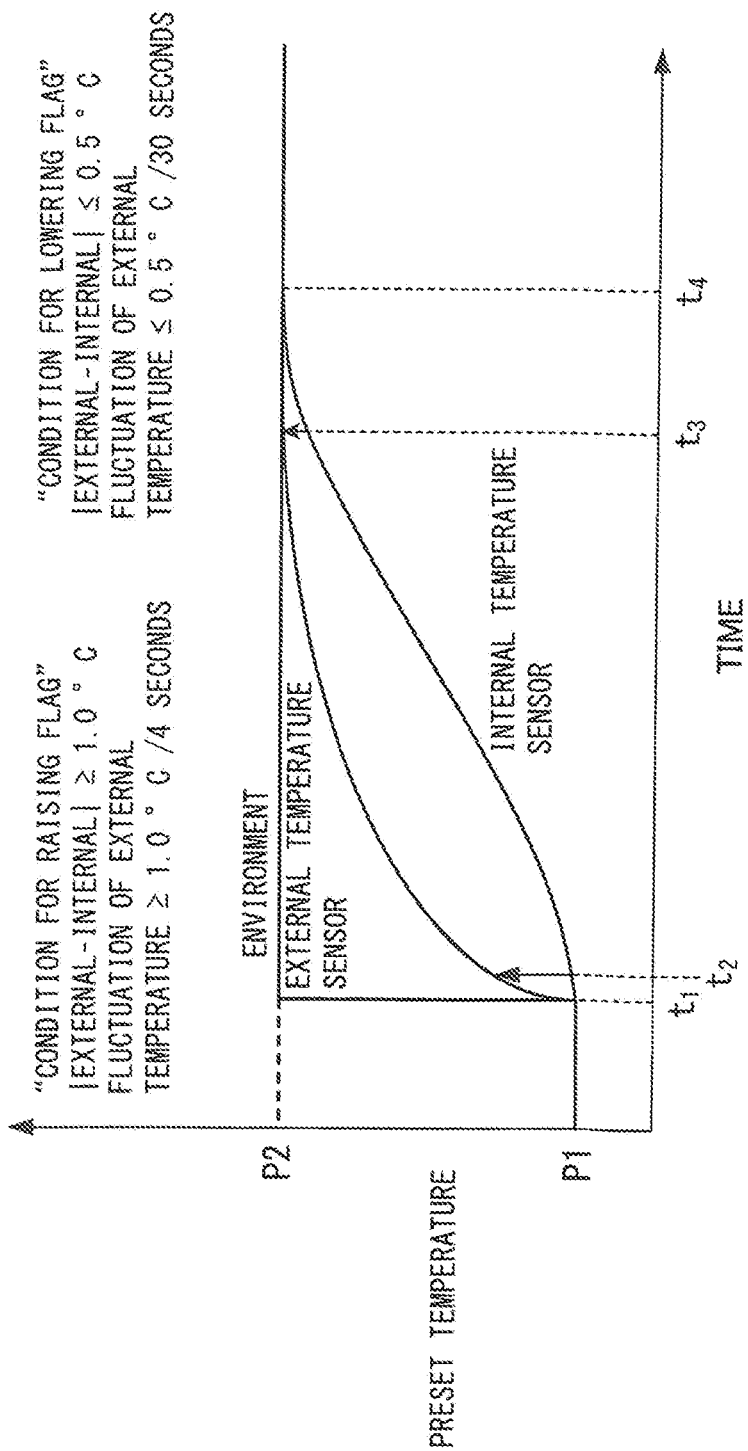
FIG. 11 is a schematic graph for explaining conditions of the temperature check processing.

FIG. 11 is a schematic graph for explaining the conditions of the temperature check processing.

The horizontal axis of the graph represents the time and the vertical axis represents the temperature.

For example, at time $t_1$, the external temperature has rapidly changed from temperature P1 to temperature P2.

Since the heat capacity of the external temperature sensor is small and, further, since the external temperature sensor is disposed at a position separated from the central portion of the case of the blood glucose meter 101 and thermally-independent from the case, the external temperature sensor rapidly becomes close to the external temperature.

On the other hand, since the internal temperature sensor is mounted on the circuit board 202 arranged in the central portion of the case of the blood glucose meter 101, the internal temperature sensor shows slow temperature change in the central portion due to slow thermal response caused by the heat capacity of the air inside the case of the blood glucose meter 101.

It is known that the temperature difference between the external temperature sensor and the internal temperature sensor becomes large in a very short time from the moment when the temperature change occurs. By using such phenomenon, the condition for raising the first flag 506 is that the temperature difference is equal to or larger than 1° C., or that the integrated value of the temperature fluctuation of the external temperature in 4 seconds is equal to or larger than 1° C.

The first flag 506 is raised at time $t_2$ after the temperature change has occurred, and then, when the temperature of the case of the blood glucose meter 101 becomes close to the external temperature, the first flag 506 is lowered (time $t_3$). It is preferred that the threshold for performing the aforesaid judgment is smaller than the threshold for raising the first flag 506. If the threshold for performing the aforesaid judgment is equal to the threshold for raising the first flag 506, the condition for raising the first flag 506 and the condition for lowering the first flag 506 will be the same, so that there is a concern that vibration may occur (i.e., operation of raising the first flag 506 and operation of lowering the first flag 506 will be repeated). To solve such problem, the condition for lowering the first flag 506 is that the temperature difference is equal to or smaller than 0.5° C., or that the integrated value of the temperature fluctuation of the external temperature in 30 seconds is equal to or smaller than 0.5° C.

Figure 12:
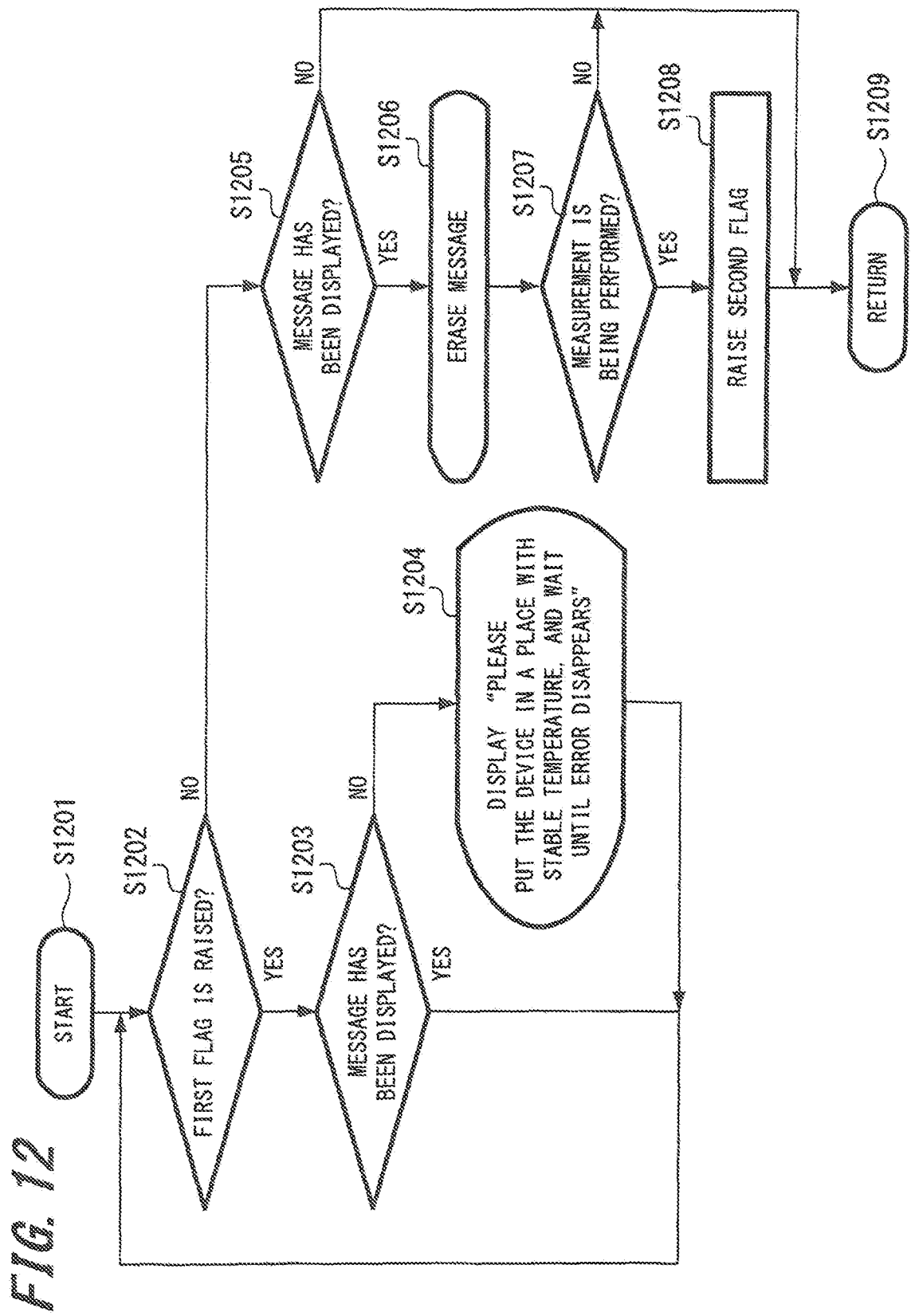
FIG. 12 is a flowchart showing exception-judging processing.

FIG. 12 is a flowchart showing the exception-judging processing. The exception-judging processing is the processing details of the controller 515 shown in FIG. 5.

As has been described with reference to FIG. 5, the controller 515 continues to monitor the states of the first flag 506 and the second flag 507, and controls the executions of the tip mounting processing section 512, the blood spotting standby processing section 513 and the measurement processing section 514. At this time, upon receiving the request for the exception-judging processing from the tip mounting processing section 512, the blood spotting standby processing section 513 and the measurement processing section 514, the controller 515 performs the exception-judging processing, and returns control to the invoker or waits until predetermined condition is satisfied without returning control, depending on the result of the exception-judging processing.

When the processing is started (S1201), the controller S15 checks whether or not the first flag 506 is raised (S1202).

If the first flag 506 is raised ("Yes" in the step S1202), the temperature check processing section 504 will judge that the temperature fluctuation has exceeded the acceptable range suitable for measuring blood glucose level. Next, the controller 515 confirms whether or not a warning message has been displayed on the LCD display section 415 (S1203). If the warning message has not been displayed ("No" in the step S1203), the controller 515 will display a warning message "please put the device in a place with stable temperature, and wait until error disappears" on the LCD display section 415 (S1204).

After the warning message has been displayed on the LCD display section 415 in the step S1204, the controller 515 checks the state of the first flag 506 again (S1202). The temperature check processing section 504 is measuring the external temperature and the internal temperature, and the internal temperature changes more slowly than the external temperature. For this reason, the temperature fluctuation judged by the temperature check processing section 504 does not quickly quiet down. As a result, the controller 515 continues to perform the loop in the steps S1202 and S1203 until the internal temperature becomes close to the external temperature.

When the internal temperature becomes close to the external temperature, the temperature fluctuation falls within the acceptable range. Thus, the temperature check processing section 504, which is performed once each second, lowers the first flag 506.

In the step S1202, if the first flag 506 is not raised ("No" in the step S1202), the temperature check processing section 504 will judge that the temperature fluctuation falls within the acceptable range suitable for measuring blood glucose level. In other words, at this point, it is at last possible to get out from the loop of the steps S1202 and S1203. Next, the controller 515 confirms whether or not the warning message has been displayed on the LCD display section 415 (S1205). If the warning message has been displayed ("Yes" in the step S1205), the controller 515 will erase the message displayed on the LCD display section 415 (S1206).

Next, the controller 515 confirms whether or not the measurement processing is being performed currently (S1207). If it is confirmed that the measurement processing is being performed currently ("Yes" in the step S1207), the controller 515 will raise the second flag 507 (S1208), and return the processing to the invoker (1209).

Incidentally, in the case where the warning message is not displayed in the step S1205 ("No" in the step S1205) and in the case where the measurement is not being performed in the step S1207 ("No" in the step S1207), the controller 515 will return the processing to the invoker without doing any thing (S1209).

As has been described with reference to FIGS. 7, 8 and 9, the exception-judging processing is performed between respective processing which constitute the overall processing. The processing will move forward with the next processing without incident as long as the temperature fluctuation falls within the acceptable range. However, if the temperature fluctuation exceeds the acceptable range, the steps S1202 and S1203 of the exception-judging processing will be repeated in loop, and it will be not possible to get out from the loop so as to move forward with the next processing until the temperature fluctuation falls within the acceptable range.

Further, the exception-judging processing invoked in the measurement processing shown in FIG. 9 is performed during the measurement processing. If the temperature fluctuation occurs during the measurement processing, there is a possibility that the blood glucose measurement value obtained at this time may include large error, and therefore the measurement value can not be used as correct measurement value. Thus, it is necessary to stop the blood glucose measurement processing.

Therefore, the exception-judging processing includes the processing of raising the second flag 507 which indicates that the temperature fluctuation has occurred during the measurement processing.

If the temperature fluctuation occurs during the measurement processing, the warning message will be displayed in the step S1204. If the temperature fluctuation has quieted down, the warning message will be erased in the step S1206, the processing of "erasing the warning message" means the fact that the temperature fluctuation had occurred right before. Thus, right after the step S1206, it is confirmed whether or not the measurement is being performed (S1207), and if it is confirmed that the measurement is been performed, the second flag 507 will be raised (S1208).

The following applications are considered in the present embodiment.

(1) If the exception-judging processing is only invoked from the tip mounting processing and the blood spotting standby processing, and in the measurement processing, a measurement stopping processing different from the exception-judging processing is performed, the second flag 507 will be unnecessary.

Figure 13:
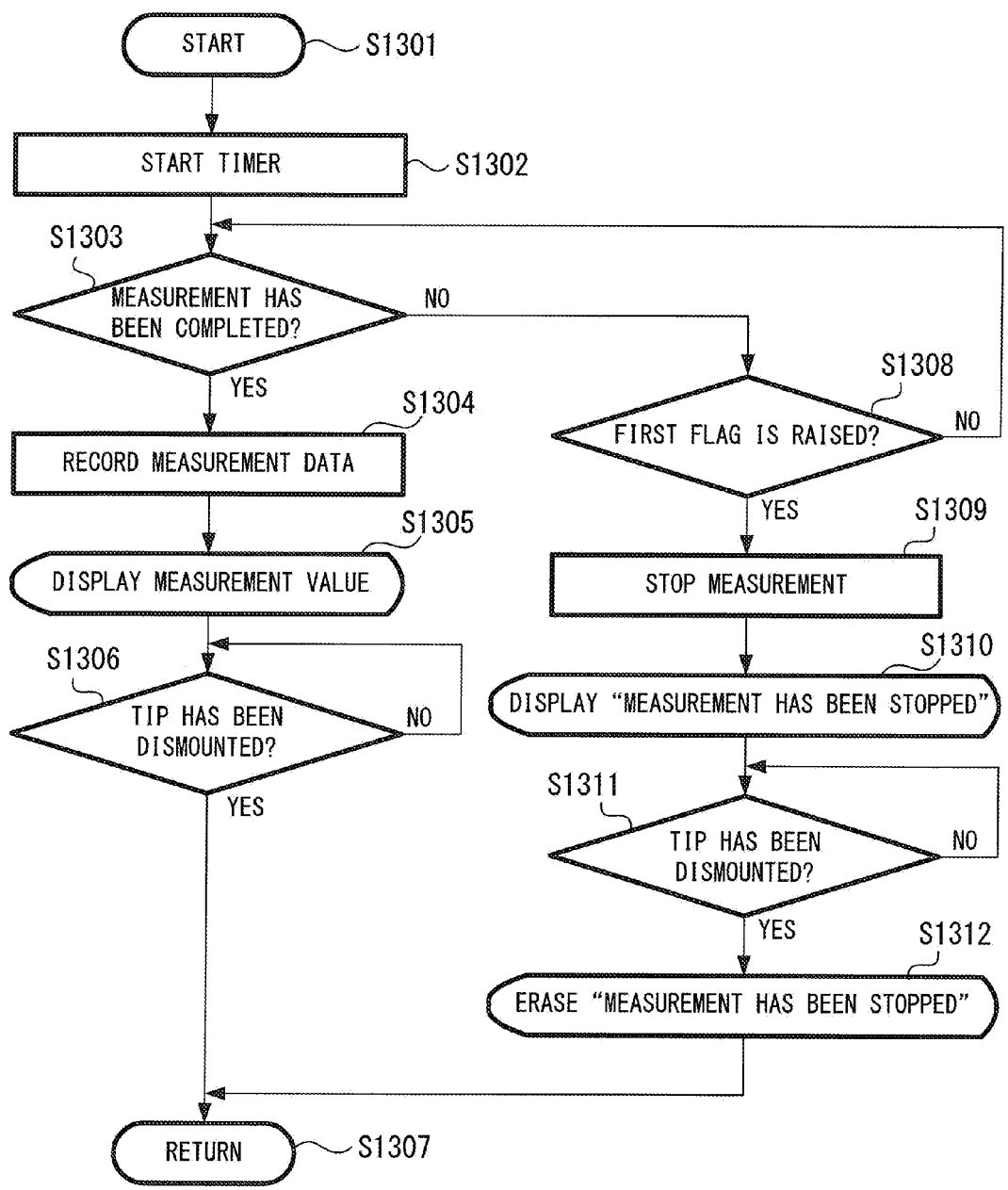
FIG. 13 is a flowchart showing measurement processing according to another embodiment of the present invention.

FIG. 13 is a flowchart showing the measurement processing according to another embodiment of the present invention; and FIG. 14 is a flowchart showing the exception-judging processing according to the same embodiment. The measurement processing of FIG. 9 and the exception-judging processing of FIG. 12 can be replaced by the flowchart of FIG. 13 and the flowchart of FIG. 14 respectively.

The difference between FIG. 13 and FIG. 9 will be described below.

If it is confirmed in the step S1303 that the measurement has not been completed based on the measurement time ("No" in the step S1303), the 514 will confirm whether or not the first flag 506 is raised (S1308). If the first flag 506 is not raised ("No" in the step S1308), since the temperature fluctuation falls within the acceptable range, the measurement processing section 514 will pass through the step S1308 to substantially perform the loop processing of the step S1303.

If it is confirmed in the step S1308 that the first flag 506 is raised ("Yes" in the step S1308), the measurement processing section 514 will move forward with the processing to be performed in the case where the measurement processing of the blood glucose level has failed.

First, the measurement processing section 514 stops the measurement operation (S1309). To be specific, the measurement processing section 514 stops the timer started in the step S1302 to stop outputting the driving control data of the LED 303 having been outputted to the D/A converter 411. Further, the measurement processing section 514 also stops the operation of the A/D converter 413b to stop reading the data based on the output current of the photodiode 304. Further, the measurement processing section 514 records information that indicates "measurement failure" to the nonvolatile storage 414.

Next, the measurement processing section 514 displays a character string "measurement has been stopped" on the LCD display section 415 (S1310). Further, the measurement processing section 514 continues to confirm whether or not the used measuring tip 308 has been dismounted from the optical measuring section 103 (S1311).

If it is confirmed that the measuring tip 308 has been dismounted ("Yes" in the step S1311), the measurement processing section 514 will erase the character string "measurement has been stopped" displayed on the LCD display section 415 (S1312). Further, the measurement processing section 514 terminates the sequence of processing and returns to the overall processing (S1307).

Different from FIG. 9, in FIG. 13, the measurement processing section 514 directly confirms the first flag 506 without invoking exception-judging processing, and if the first flag 506 is raised, the measurement processing section 514 will immediately stop the measurement operation. Thus, in the measurement processing shown in FIG. 13, the warning message "please put the device in a place with stable temperature, and wait until error disappears" displayed in the exception-judging processing is not displayed on the LCD display section 415.

The difference between FIG. 14 and FIG. 12 will be described below.

In the step S1402, if the first flag 506 is not raised ("No" in the step S1402), it will be judged by the temperature check processing section 504 that the temperature fluctuation falls within the acceptable range suitable for measuring blood glucose level. Next, the controller 515 confirms whether or not the warning message has been displayed on the LCD display section 415 (S1405). If the warning message has been displayed ("Yes" in the step S1405), the controller 515 will erase the message displayed on the LCD display section 415 (S1406). Further, the controller 515 terminates the sequence of processing (S1407).

Incidentally, in the case where the warning message is not displayed in the step S1405 ("No" in the step S1405), the controller 515 will return the processing to the invoker without doing any thing (S1407).

Different from FIG. 12, the flowchart of FIG. 14 has no step of confirming whether or not the measurement is being performed and operating the second flag 507.

The operation of the blood glucose meter 101 in the case where the aforesaid processing steps are replaced by processing steps of the flowchart of FIG. 13 and FIG. 14 will be described below.

If the temperature fluctuation exceeds the acceptable range during the measurement processing, it will be confirmed that the first flag 506 has been raised in the step S1308 of FIG. 13, so that the measurement will be stopped in the step S1309. If the measuring tip 308 is dismounted in the step S1311, the processing will be returned to the overall processing in the step S1307. However, the processing flow from the step S1308 to the step S1307 through the step S1312 does not include the processing of displaying the warning message "please put the device in a place with stable temperature, and wait until error disappears" on the LCD display section 415 and the processing of continuing to wait by performing loop until the first flag 506 is lowered, which are included in the exception-judging processing. In other words, there is a high possibility that, when the measurement fails and the measuring tip is dismounted from the optical measuring section 103, the temperature fluctuation has not yet fallen within the acceptable range.

Such processing is performed at the exception-judging processing performed in the first stage of the tip mounting processing, following the last measurement processing (i.e., the step S709a in FIG. 7).

As can be known from the above description, even if the processing of FIG. 9 and the processing of FIG. 12 are respectively replaced by the content of the flowchart of FIG. 13 and the content of the flowchart of FIG. 14, the same advantages can be achieved substantially.

(2) The aforesaid embodiment is described based on a blood glucose meter for hospital ward; however, the same embodiment may also be applied to a simplified blood glucose meter for self-measurement.

The blood glucose meter is disclosed in the present embodiment.

An internal temperature thermistor for measuring the internal temperature of the case of the blood glucose meter is arranged inside the case of the blood glucose meter, and an external temperature thermistor configured by components with low heat capacity and adapted for measuring the external temperature is arranged at a position separated from the central portion of the case of the blood glucose meter and thermally independent from the case. Further, the microcomputer of the blood glucose meter includes the following processing: judging whether or not the temperature fluctuation falls within the acceptable range based on the difference between the respective temperatures and, if the temperature fluctuation exceeds the acceptable range, temporarily stopping the processing until the temperature fluctuation falls within the acceptable range in the case where the blood glucose measurement has not yet been performed, or stopping the blood glucose measurement processing in the case where the blood glucose measurement is being performed.

By configuring the blood glucose meter in the aforesaid manner, it is possible to reliably detect the temperature fluctuation surrounding the blood glucose meter, and perform blood glucose measurement in an appropriate environment.

It is to be understood that, although the present invention is described based on the aforesaid embodiment, the present invention is not limited to the embodiment, and various modifications and applications can be made without departing from the spirit and scope of the present invention.

EXPLANATION OF REFERENCE NUMERALS 101 blood glucose meter
102 case
103 optical measuring section
104 eject lever
105 display panel
106 operation panel
202 circuit board
203 internal temperature thermistor
302 tube
303 LED
304 photodiode
305 base
306 glass window
307 external temperature thermistor
308 measuring tip
402 CPU
403 ROM
404 RAM
405 bus
407 real-time clock
408 button operating portion
410 driver
411 D/A converter
413 A/D converter
414 nonvolatile storage
415 LCD display section
R502, R503, R508, R510 voltage-dividing resistor
504 temperature check processing section
505 interrupt clock generator
506 first flag
507 second flag
509 driving transistor
511 test paper
512 tip mounting processing section
513 blood spotting standby processing section
514 measurement processing section
515 controller

The invention claimed is:

1. A blood glucose meter comprising:
a blood glucose measuring section adapted to, in a state where a measuring tip is mounted, spot blood onto the measuring tip, and output a signal corresponding to the glucose level of the blood;
a tip mounting processing section adapted to confirm whether or not the measuring tip has been mounted on the blood glucose measuring section;
a blood spotting standby processing section adapted to confirm whether or not the blood has been spotted onto the measuring tip;
a measurement processing section adapted to obtain a blood glucose value based on the signal outputted from the blood glucose measuring section;
a case in which the tip mounting processing section, the blood spotting standby processing section and the measurement processing section are housed;
an internal temperature sensor disposed inside the case;
an external temperature sensor disposed in a peripheral portion of the case separated from the internal temperature sensor;
a temperature check processing section adapted to compare temperature difference between the internal temperature sensor and the external temperature sensor with a predetermined threshold to judge whether or not the change of the ambient temperature of the case is suitable for measuring blood glucose level; and
a controller adapted to temporarily stop, if the temperature check processing section judges that it is not suitable for measuring blood glucose level when the tip mounting processing section or the blood spotting standby processing section is in operation, the processing of the tip mounting processing section or the processing of the blood spotting standby processing section until the temperature check processing section judges that it is suitable for measuring blood glucose level.

2. The blood glucose meter according to claim 1,
wherein the blood glucose measuring section is arranged in a peripheral portion of the case, and
wherein the external temperature sensor is arranged in the blood glucose measuring section.

3. The blood glucose meter according to claim 1,
wherein the temperature check processing section judges, if the temperature difference is equal to or larger than a first threshold, that the change of the ambient temperature of the case is not suitable for measuring blood glucose level, and judges, if the temperature difference is equal to or smaller than a second threshold smaller than the first threshold, that the change of the ambient temperature of the case is suitable for measuring blood glucose level.

4. The blood glucose meter according to claim 1,
wherein the temperature check processing section judges, if the integrated value of the temperature fluctuation within a last first time is equal to or larger than a third threshold, that the change of the ambient temperature of the case is not suitable for measuring blood glucose level, and judges, if the integrated value of the temperature fluctuation within a last second time longer than the last first time is equal to or shorter than a fourth threshold smaller than the third threshold, that the change of the ambient temperature of the case is suitable for measuring blood glucose level.

5. The blood glucose meter according to claim 1, wherein the controller is adapted to stop, if the temperature check processing section judges that it is not suitable for measuring blood glucose level when the measurement processing section is in operation, the processing of the measurement processing section.

6. A blood glucose measurement method comprising:
a tip mounting processing for confirming whether or not a measuring tip has been mounted on a blood glucose measuring section that is adapted to, in a state where the measuring tip is mounted, spot blood onto the measuring tip, and output a signal corresponding to glucose level of the blood;
a blood spotting standby processing for confirming, after the tip mounting processing, whether or not the blood has been spotted onto the measuring tip;
a measurement processing for obtaining, after the blood spotting standby processing, a blood glucose value based on the signal outputted from the blood glucose measuring section;
a temperature check processing for comparing, independent of the tip mounting processing, the blood spotting standby processing and the measurement processing, a temperature difference between an internal temperature sensor and an external temperature sensor with a predetermined threshold to judge whether or not the change of the ambient temperature of a case of the blood glucose meter is suitable for measuring blood glucose, and setting the judging result as a flag, wherein the internal temperature sensor is disposed inside the case, and the external temperature sensor is disposed in a peripheral portion of the case separated from the internal temperature sensor, and
a control processing invoked from the tip mounting processing and the blood spotting standby processing and adapted for temporarily stopping, if the flag shows that it is not suitable for measuring blood glucose level, the processing of the tip mounting processing or the processing of the blood spotting standby processing until the flag shows that it is suitable for measuring blood glucose level.

* * * * *